United States Patent
Müller et al.

(10) Patent No.: US 8,394,383 B2
(45) Date of Patent: Mar. 12, 2013

(54) **ALLERGENS FROM *ASPERGILLUS VERSICOLOR*, AND METHOD OF DETECTING A MOLD ALLERGY CAUSED BY INTERIOR ROOMS**

(75) Inventors: Andrea Müller, Taucha (DE); Dirk Benndorf, Leipzig (DE); Katharina Bock, Frankfurt (DE); Martin Von Bergen, Leipzig (DE); Olaf Herbarth, Leipzig (DE)

(73) Assignee: Helmholtz-Zentrum fur Umwelt-Forschung GmbH, Leipzig (DE)

( * ) Notice: Subject to any disclaimer, the term of this patent is extended or adjusted under 35 U.S.C. 154(b) by 56 days.

(21) Appl. No.: 12/667,902

(22) PCT Filed: Jul. 3, 2008

(86) PCT No.: PCT/EP2008/058581
§ 371 (c)(1),
(2), (4) Date: Sep. 7, 2010

(87) PCT Pub. No.: WO2009/007298
PCT Pub. Date: Jan. 15, 2009

(65) Prior Publication Data
US 2011/0052638 A1 Mar. 3, 2011

(30) Foreign Application Priority Data
Jul. 6, 2007 (DE) .......................... 10 2007 031 947

(51) Int. Cl.
*A61K 39/35* (2006.01)
*C07H 21/00* (2006.01)
*G01N 33/53* (2006.01)

(52) U.S. Cl. ..................... 424/185.1; 435/7.1; 536/23.2; 536/23.74

(58) Field of Classification Search .................... None
See application file for complete search history.

(56) References Cited

FOREIGN PATENT DOCUMENTS

| | | |
|---|---|---|
| EP | 1104768 A | 6/2001 |
| WO | 2004/108765 A | 12/2004 |
| WO | 2005/003310 A | 1/2005 |
| WO | 2006/097539 A | 9/2006 |

OTHER PUBLICATIONS

Stadler et al. (FASEB J., 17:1141-1143, 2003).*
Horner et al. (Immunologic. Rev., 179:102-118, 2001).*
Benndorf D et al: "Identification of spore allergens from the indoor mould *Aspergillus versicolor*" Allergy, Munskgaard, Copenhagen,Bd. 63, Nr. 4, Apr. 1, 2008, pp. 454-460.
Bock K et al: "Identification of allergens from the indoor mold *Aspergillus versicolor*" Allergy, Munskgaard, Copenhagen, Bd. 63, Nr. suppl. 88, Jun. 11, 2008, pp. 530-531.
Hansen M Y et al: "Allergens in *Apsergillus fumigatus*: I. Characterization of Two Different Allergen Extracts and Evaluation of Their Stability and the Importance of Carbohydrate for IGE Binding" Allergy, Munskgaard, Copenhagen, Bd. 49, Nr. 4, Jan. 1, 1994, pp. 235-241.
Verma J et al: "Studies on shared antigenic/allergenic components among fungi" Allergy, Munskgaard, Copenhagen, Bd. 50, Nr. 10, Oct. 1, 1995, pp. 811-816.
Database EMBL [Online], Aug. 30, 2000, "*Aspergillus oryzae* gpdA mRNA for glyceraldehyde-3-phosphate dehydrogenase, complete cds."
Database UniProt [Online], Mar. 6, 2007, "SubName: Full=Catalytic activity: R-CHOH-R' + NADP(+) <=> R-CO-R' + NADPH.; EC=<A HREF="http://srs.ebi.ac.uk/srsbinicgi-bin/wgetz?[enzyme-ECNumber:1.1.1.184]+-e">1.1.1.184</A>;".
Singh A B et al: "Common environmental allergens causing respiratory allergy in India" Indian Journal of Pediatrics, All India Institute of Medical Sciences, New Dehli, IN, Bd. 69, Nr. 3, Mar. 1, 2002, pp. 245-250.
Database UniProt [Online] Jul. 5, 2005, "SubName: Full=Sorbitol/xylulose reductase Sou1-like, putative; EC=<A HREF="http://srs.ebi.ac.uk/srsbin/cgi-bin/ wgetz?[enzyme-ECNumber:1.*.*.*]+-e">1.-.-.-</A>".
Rydjord B et al: "Immunoglobulin G antibodies against environmental moulds in a Norwegian healthy population shows a bimodal distribution for *Aspergillus versicolor*" Scandinavian Journal of Immunology, Blackwell Science Publ., Oxford, GB, Bd. 62, Nr. 3, Sep. 1, 2005, pp. 288-281.

* cited by examiner

*Primary Examiner* — Brian J Gangle
(74) *Attorney, Agent, or Firm* — Norris McLaughlin & Marcus, P.A.

(57) ABSTRACT

The invention relates to seven allergens of *Aspergillus versicolor* which are suitable for specific diagnostics of this mold which predominantly pollutes the interior. The invention is also directed to an immunological method of detecting a sensitization to *A. versicolor*, especially an allergy, wherein one or more of the above-mentioned seven allergens found are employed as diagnostic markers. The invention further relates to a pharmaceutical composition which includes one or more of these seven allergens as active substance, and to the use of one or more of these seven allergens for the desensitization to *A. versicolor*.

8 Claims, 3 Drawing Sheets

SEQUENCE LISTING

<160> NUMBER OF SEQ ID NOS: 4

<210> SEQ ID NO 1
<211> LENGTH: 336
<212> TYPE: PRT
<213> ORGANISM: Aspergillus versicolor

<400> SEQUENCE: 1

| Met | Ala | Pro | Lys | Val | Gly | Ile | Asn | Gly | Phe | Gly | Arg | Ile | Gly | Arg | Ile |
|---|---|---|---|---|---|---|---|---|---|---|---|---|---|---|---|
| 1 | | | | 5 | | | | | 10 | | | | | 15 | |

| Val | Phe | Arg | Asn | Ala | Ile | Glu | Asp | Ser | Val | Asp | Val | Ile | Ala | Val |
|---|---|---|---|---|---|---|---|---|---|---|---|---|---|---|
| | | | 20 | | | | | 25 | | | | | 30 | |

Asn Asp Pro Phe Ile Glu Thr His Tyr Ala Ala Tyr Met Leu Lys Tyr
            35                  40                  45

Asp Ser Gln His Gly Gln Phe Lys Gly Thr Ile Glu Thr Tyr Asp Gln
        50                  55                  60

Gly Leu Val Val Asn Gly Lys Lys Ile Arg Phe Phe Thr Glu Arg Asp
65                  70                  75                  80

Pro Ala Ser Ile Pro Trp Gly Gln Ala Gly Ala Asp Tyr Ile Val Glu
                85                  90                  95

Ser Thr Gly Val Phe Thr Thr Gln Glu Lys Ala Gly Ala His Leu Lys
            100                 105                 110

Gly Gly Ala Lys Lys Val Ile Ile Ser Ala Pro Ser Ala Asp Ala Pro
        115                 120                 125

Met Phe Val Met Gly Val Asn Asn Glu Thr Tyr Lys Lys Asp Val Gln
130                 135                 140

Ile Leu Ser Asn Ala Ser Cys Thr Thr Asn Cys Leu Ala Pro Leu Ala
145                 150                 155                 160

Lys Val Ile Asn Asp Asn Phe Gly Ile Ile Glu Gly Leu Met Thr Thr
                165                 170                 175

Val His Ser Tyr Thr Ala Thr Gln Lys Val Val Asp Gly Pro Ser Ala
            180                 185                 190

Lys Asp Trp Arg Gly Gly Arg Thr Ala Ala Thr Asn Ile Ile Pro Ser
        195                 200                 205

Ser Thr Gly Ala Ala Lys Ala Val Gly Lys Val Ile Pro Ser Leu Asn
210                 215                 220

Gly Lys Leu Thr Gly Met Ala Met Arg Val Pro Thr Ser Asn Val Ser
225                 230                 235                 240

Val Val Asp Leu Thr Val Arg Thr Glu Lys Gly Val Thr Tyr Asp Gln
                245                 250                 255

Ile Lys Glu Ala Ile Lys Lys Ala Ser Asp Asn Glu Leu Lys Gly Ile
            260                 265                 270

Leu Gly Tyr Thr Glu Asp Ile Val Ser Thr Asp Leu Asn Gly Asp
        275                 280                 285

Thr Arg Ser Ser Ile Phe Asp Ala Lys Ala Gly Ile Ala Leu Asn Ala
290                 295                 300

Asn Phe Ile Lys Leu Val Ser Trp Tyr Asp Asn Glu Trp Gly Tyr Ser
305                 310                 315                 320

Arg Arg Val Val Asp Leu Ile Ser Tyr Ile Ala Lys Val Asp Gly Gln
                325                 330                 335

<210> SEQ ID NO 2
<211> LENGTH: 1011
<212> TYPE: DNA
<213> ORGANISM: Aspergillus versicolor

<400> SEQUENCE: 2
atggctccca aggttggaat caacggcttc ggtcgtatcg acgtattgt cttccgtaac      60 gccatcgagg ctgactccgt cgatgtcatc gccgtcaacg acccttcat tgagacccac     120 tacgctgcct acatgctcaa gtatgacagt cagcacggtc agttcaaggg caccatcgag     180

```
acctacgacc agggcctcgt tgtcaacggc aagaagatcc gcttcttcac cgagcgtgac    240
cctgccagca tcccttgggg ccaggctggc gccgactaca ttgtcgagtc tactggtgtt    300
ttcaccacgc aggagaaggc tggcgctcac ttgaagggtg gtgccaagaa ggtcatcatc    360
tctgctcctt ccgctgatgc ccccatgttc gtcatgggcg tcaacaacga gacgtacaag    420
aaggacgtcc aaatcctctc caacgcttct tgcaccacca actgccttgc ccctctcgcc    480
aaggttatca cgacaacctt cggtattatt gagggtctga tgacaaccgt ccactcctac    540
actgctaccc agaaggtcgt cgatggcccc tccgccaagg actggcgtgg tggccgtacg    600
gccgctacca acatcatccc cagctctact ggtgctgcca aggctgtcgg caaggttatt    660
ccttcgctca acggcaagct cactggaatg gccatgcgtg ttcccacctc caacgtctct    720
gttgttgact tgaccgtccg caccgagaag ggcgtcacct acgaccagat caaggaggcc    780
atcaagaagg cttccgacaa cgagctcaag ggcatccttg ctacaccga ggatgacatt     840 gtctccactg acctgaacgg tgacacccgc tcttccatct tcgatgccaa ggctggtatt    900
gctctcaacg ccaacttcat caagctcgtt tcctggtacg acaacgagtg gggttactcc    960
cgccgtgttg ttgacctcat ctcctacatt gccaaggtcg atggccaata g           1011
```

<210> SEQ ID NO 3
<211> LENGTH: 266
<212> TYPE: PRT
<213> ORGANISM: Aspergillus versicolor

<400> SEQUENCE: 3

```
Met Pro Gln Gln Ile Pro Thr Ser Ser His Leu Gln Asp Leu Phe Ser
1               5                   10                  15

Leu Lys Gly Lys Val Val Val Thr Gly Ala Ser Gly Pro Arg Gly
            20                  25                  30

Met Gly Ile Glu Ala Ala Arg Gly Cys Ala Glu Met Gly Ala Asn Val
        35                  40                  45

Ala Ile Thr Tyr Ser Ser Arg Pro Glu Gly Gly Glu Lys Asn Ala Glu
    50                  55                  60

Glu Leu Ser Arg Asp Phe Gly Ile Lys Ala Lys Ala Tyr Lys Leu Asp
65                  70                  75                  80

Ile Gly Asn Tyr Glu Ser Val Glu Lys Leu Val Lys Asp Val Ile Ala
                85                  90                  95

Glu Phe Gly Gln Ile Asp Ala Phe Ile Ala Asn Ala Gly Arg Thr Ala
            100                 105                 110

Asn Ser Gly Ile Leu Asp Gly Ser Val Lys Asp Trp Glu Glu Val Val
        115                 120                 125

Gln Thr Asp Leu Thr Gly Thr Phe His Cys Ala Lys Ala Val Gly Pro
    130                 135                 140

His Phe Lys Gln Arg Gly Ser Gly Ser Leu Val Ile Thr Ala Ser Met
145                 150                 155                 160

Ser Gly His Ile Ala Asn Phe Pro Gln Glu Gln Thr Ser Tyr Asn Val
                165                 170                 175

Ala Lys Ala Gly Cys Ile His Met Ala Arg Ser Leu Ala Asn Glu Trp
            180                 185                 190

Arg Asp Phe Ala Arg Val Asn Ser Ile Ser Pro Gly Tyr Ile Asp Thr
        195                 200                 205

Gly Leu Ser Asp Phe Val Asp Lys Lys Val Gln Asp Leu Trp Leu Ser
    210                 215                 220

Met Ile Pro Met Gly Arg Asn Gly Asp Ala Lys Glu Leu Lys Gly Ala
225                 230                 235                 240
```

```
Tyr Val Tyr Leu Val Ser Asp Ala Ser Thr Tyr Thr Thr Gly Ala Asp
                245                 250                 255

Leu Val Ile Asp Gly Gly Tyr Thr Val Arg
            260                 265

<210> SEQ ID NO 4
<211> LENGTH: 801
<212> TYPE: DNA
<213> ORGANISM: Aspergillus versicolor

<400> SEQUENCE: 4
atgccgcagc aaatccccac ctcctcccac ctccaagacc tgttcagcct aaagggcaag      60
gtcgtcgtcg tcactggtgc ctctggcccc cgtggcatgg gcattgaagc tgcccgcggc     120
tgtgccgaaa tgggcgccaa cgttgcaatc acctactcct cccgccccga gggcggcgag     180
aagaacgccg aagagctatc ccgcgacttc ggcatcaagg ccaaggccta caagcttgac     240
atcggcaact acgaaagcgt agagaagcta gtgaaggatg tgatcgcaga attcggacaa     300
attgacgctt tcatcgcgaa tgccggacgt accgcgaact cgggtatcct ggacggctca     360
gtcaaggact gggaggaggt ggtacagacg gatttgacgg gaacgttcca ctgcgcgaag     420
gctgtggggc cgcactttaa gcagcgcggt tcgggcagtc tcgttatcac cgccagtatg     480
agtgggcaca ttgccaactt cccgcaagag cagacgagtt ataacgttgc gaaggctgga     540
tgtattcaca tggcccggtc gttggcgaat gagtggaggg actttgcgcg tgtcaactcc     600
atctcgcctg gttacattga taccgggttg agtgactttg tggataagaa ggttcaggac     660
ctctggctta gcatgatccc tatgggccga aacggtgatg cgaaggagtt gaagggtgcc     720
tatgtctact tggtcagtga tgccagtact tacacaactg gtgcagacct tgtcattgac     780
ggtggataca ctgtgcggta a                                               801
```

ALLERGENS FROM ASPERGILLUS VERSICOLOR, AND METHOD OF DETECTING A MOLD ALLERGY CAUSED BY INTERIOR ROOMS

This application is a 371 application of PCT/EP2008/0058581 filed Jul. 3, 2008, which claims priority to the German application 10 2007 031 947.0 filed Jul. 6, 2007.

The invention relates to seven allergens of *Aspergillus versicolor* which are suitable for specific diagnostics and for the sensitization to this mold which predominantly pollutes the interior. The invention is also directed to an immunological method of detecting a sensitization to *A. versicolor*, especially an allergy, wherein one or more of the above-mentioned seven allergens found are employed as diagnostic markers. The invention further relates to a pharmaceutical composition which includes one or more of these seven allergens as active substance, and to the use of one or more of these seven allergens for the desensitization to *A. versicolor*.

Today, the health of humans is being more and more impaired by allergies. Triggers of allergic reactions can be both natural and artificial substances. Apart from genetic disposition, the so-called lifestyle plays an important role in the development of allergies. People in modern industrial nations spend a large amount of their time in living-rooms and workrooms, and the quality of the indoor air represents an important factor for their well-being. Faulty constructions and insufficient ventilation may result in indoor mold colonization and may directly impair the health of occupants because mold growth leads to liberation of mold spores which may reach high concentrations in the indoor air. In addition to mycoses in immunodeficient patients or mycotoxicoses caused by mold toxins, molds can trigger allergies. Probably more than 5% of the German population is affected by a mold allergy.

The allergenic effect is caused by proteins located in the spores of molds and entering the human organism mainly via the respiratory tract to potentially cause respiratory ailments and impaired well-being. Development of a mold allergy is promoted by frequently staying indoors and the thus-increased exposition to allergens, especially during the cold season. The pollution caused by molds can either be detected by investigating the visible mold or by determining the spore concentration in air or dust samples. Various studies have shown that apart from the highly pathogenic *A. fumigatus*, *Aspergillus versicolor* frequently occurs indoors. Possible sensitization of patients to molds is determined in the prick test or by determining specific IgEs. Currently marketed well-known diagnostic kits cover a relatively large spectrum of diet- and environment-specific molds, but just not those types having particular indoor relevance.

Despite the frequent indoor occurrence of *A. versicolor*, nothing is known about its allergens and there are no specific tests for detecting an allergy to *A. versicolor*. To date, no allergens of *A. versicolor* have been deposited in the recognized allergen data base of Allergome (www.allergome.org). Up to now it has been unknown in the art that *A. versicolor* has any proteins at all that would be suitable as allergens. On the contrary, Sing et al. have reported e.g. that none of the serums of 19 individuals working in a bakery, none of the serums of 53 atopic patients and none of the serums of 15 healthy control subjects gave a specific reaction with a protein fraction of *A. versicolor*, whereas such reactions were detectable in the other investigated *Aspergillus* species, especially in *A. fumigatus* (Singh et al., Sensitization to different species of *Aspergillus* in bakery workers and general atopic population, Asian Pacific Journal of Allergy and Immunology (1998) 16, 5-15). Up to the present it has been assumed that *A. versicolor* has no suitable allergens which would be specific to these species and could be utilized for diagnostics or sensitization. According to the general understanding, *A. versicolor* is not suitable for searching new allergens.

Three major allergens and four additional allergens of *A. versicolor* have now been found which are located in the spores and, surprisingly, have been unknown as allergens of any other mold. Consequently, they have neither been covered in allergy testing for *Aspergillus fumigatus*. These seven inventive marker antigens of *Aspergillus versicolor* now permit specific diagnostics of *A. versicolor* so that the diagnostics of allergies to indoor-relevant molds can be significantly improved.

The invention is directed to the seven proteins found that are illustrated in Table 1 and FIG. 3. Preferred proteins are selected from the group comprising a glyceraldehyde-3-phosphate dehydrogenase (GAPDH; Asp a, b, c) with the amino acid sequence SEQ ID No. 1 or parts thereof as long as these parts are not identical to parts of the amino acid sequence of GAPDH of *Aspergillus fumigatus*, a hypothetical xylol/sorbitol reductase with the amino acid sequence SEQ ID No. 3 or parts thereof as long as these parts are not identical to parts of the amino acid sequence of the corresponding protein of *Aspergillus fumigatus* having the genebank accession number gi/71002394/ref/XP_755878.1, a katalase A with a molecular weight of 84,108 Daltons and an isoelectric point of 6.02 (Asp e), a protein with a molecular weight of 26,713 Daltons and an isoelectric point of 6.53 (Asp f), an enolase with a molecular weight of 47,519 Daltons and an isoelectric point of 5.37 (Asp g), a protein with a molecular weight of 22,007 Daltons and an isoelectric point of 5.85 (Asp h), a malate dehydrogenase with a molecular weight of 35,764 Daltons and an isoelectric point of 8.82 (Asp i).

The proteins with SEQ ID No. 1 and SEQ ID No. 3 have a sequence identity to their homologs from *Aspergillus fumigatus* of 83% and 82%, respectively.

In a preferred fashion the allergens of *Aspergillus versicolor* are selected from the group comprising a glyceraldehyde-3-phosphate dehydrogenase (GAPDH; allergen designation Asp a, b, c) with the amino acid sequence SEQ ID No. 1 or parts thereof as long as these parts are not identical to parts of the amino acid sequence of GAPDH from *Aspergillus fumigatus* and a hypothetical xylol/sorbitol reductase (protein AO090012000287; allergen designation Asp d) with the amino acid sequence SEQ ID No. 3 or parts thereof as long as these parts are not identical to parts of the amino acid sequence of the corresponding protein of *Aspergillus fumigatus* with the genebank accession number gi/71002394/ref/XP_755878.1.

In the meaning of the present invention the term "allergens of *Aspergillus versicolor*" comprises not only allergens directly isolated or recovered from *A. versicolor*, spores or parts or homogenizates thereof, but also allergens produced synthetically or by means of genetic engineering.

The proteins and allergens according to the invention are particularly suitable for use as diagnostic markers for the in vitro detection of a mold allergy to *A. versicolor*, as medicaments, and for the desensitization to *A. versicolor*.

The invention is also directed to nucleic acids including at least one nucleic acid sequence which encodes an allergen according to the invention. Preferred nucleic acids include a sequence selected from a nucleic acid sequence with SEQ ID No. 2 which encodes the allergen with SEQ ID No. 1 and a nucleic acid sequence with SEQ ID No. 4 which encodes the allergen with SEQ ID No. 3. Nucleic acids according to the invention can be natural or artificial nucleic acids. They can be constituted of DNA or RNA or derivatives thereof or may include the same. Nucleic acids according to the invention also comprise nucleic acids which bear a nucleic acid sequence encoding one of the allergens and additional sequence sections which permit transport of the nucleic acid into a cell or a microorganism by means of genetic engineering, such as a suitable vector system. Those skilled in the art will be familiar with suitable vector systems and techniques of producing and cloning nucleic acids according to the invention.

The invention also relates to a method for the preparation of one or more of these allergens. A preferred method uses nucleic acids according to the invention. Nucleic acids encoding an allergen of the invention can be cloned into a suitable vector system, for example, which is subsequently used to transfect or transform a suitable cell or microorganism. The genetically modified cells or microorganisms thus produced will express the desired allergen. Optionally, the allergen can subsequently be isolated and/or purified. A particularly preferred method for the preparation of one or more allergens comprises the steps of:
a) using a nucleic acid according to the invention,
b) transforming a microorganism or transfecting a cell with a nucleic acid including a nucleic acid of the invention, and
c) optionally purifying the produced allergen.

The allergens or the genetically modified cells or microorganisms thus produced are particularly suitable for further uses according to the invention.

The invention is directed to genetically modified cells or microorganisms including at least one nucleic acid according to the invention.

The invention is also directed to an immunological method for the in vitro detection of a mold allergy to *A. versicolor*, which method is characterized in that the allergens found are used to detect *A. versicolor*-specific IgE and/or IgG antibodies in a sample of body fluid by binding to these specific allergens. The inventive detection of the specific IgE and/or IgG antibodies preferably proceeds in an enzyme immunoassay or radioimmunoassay, with antibodies or aptamers or derivatives thereof preferably being used for detection in an assay according to the invention.

In a particularly preferred fashion the ELISA solid phase technique is used. To this end, the allergen(s) according to the invention is/are bound to a solid phase, incubated with the patient samples containing the specific IgE and/or IgG antibodies to be detected, and binding is detected via enzyme- or fluorescence-labeled secondary antibodies or secondary aptamers against the antibodies of the patient (anti-IgE and/or anti-IgG antibodies). For example, peroxidase, alkaline phosphatase, or galactosidase enzymes and suitable substrates can be used as detection system.

It is of course also possible to enhance the signals by binding a plurality of secondary antibodies or secondary aptamers to the IgE/IgG primary antibodies. Moreover, the use of streptavidin and biotinylated marker enzyme permits linkage of a relatively large number of enzyme molecules to an antibody molecule.

According to the invention, the body fluid sample can be blood, serum, plasma, urine, cerebrospinal fluid, or saliva, and serum samples are used in particular.

The *A. versicolor* allergens according to the invention were usually obtained and identified in such a way that the spore proteins of *A. versicolor* were separated using one- and two-dimensional electrophoresis, blotted and detected with the IgE antibodies contained in patient serum. The allergens according to the invention were cut out of the 2D gels, tryptically digested, and identified by means of mass spectrometry. For use in diagnostics and therapy, the allergens were purified from spore extracts using chromatographic methods. Overexpression in *E. coli* or *Pichia pastoris* (or other expression systems) of the genes to be sequenced and coupling to tags such as His-tag or Strep-tag during expression facilitate purification and preparation of relatively large amounts of the allergens.

In a particularly preferred fashion the method according to the invention uses allergens selected from the group comprising a glyceraldehyde-3-phosphate dehydrogenase (GAPDH; allergen designation Asp a, b, c) with the amino acid sequence SEQ ID No. 1 or parts thereof as long as these parts are not identical to parts of the amino acid sequence of GAPDH from *Aspergillus fumigatus* and a hypothetical xylol/sorbitol reductase (protein AO090012000287; allergen designation Asp d) with the amino acid sequence SEQ ID No. 3 or parts thereof as long as these parts are not identical to parts of the amino acid sequence of the corresponding protein of *Aspergillus fumigatus* with the genebank accession number gi/71002394/ref/XP_755878.1.

The invention is also directed to the use of one or more of the allergens according to the invention as diagnostic markers for the in vitro detection of a mold allergy to *A. versicolor*. As diagnostic markers it is particularly preferred to use allergens selected from the group comprising a glyceraldehyde-3-phosphate dehydrogenase (GAPDH; allergen designation Asp a, b, c) with the amino acid sequence SEQ ID No. 1 or parts thereof as long as these parts are not identical to parts of the amino acid sequence of GAPDH from *Aspergillus fumigatus* and a hypothetical xylol/sorbitol reductase (protein AO090012000287; allergen designation Asp d) with the amino acid sequence SEQ ID No. 3 or parts thereof as long as these parts are not identical to parts of the amino acid sequence of the corresponding protein of *Aspergillus fumigatus* with the genebank accession number gi/71002394/ref/XP_755878.1.

The invention also relates to a pharmaceutical composition comprising as active component at least one component selected from the group comprising one or more allergens according to the invention, lysate of mycelium or spores of *A. versicolor*, a nucleic acid according to the invention or a genetically modified cell or microorganism including such an inventive nucleic acid. The pharmaceutical composition is used for the desensitization to *A. versicolor*. In addition to the active component(s), the pharmaceutical composition includes conventional auxiliary agents, especially carriers and/or adjuvants. The pharmaceutical composition of the invention is preferably provided as injection or infusion solution, e.g. as an aqueous solution or an aqueous or oily suspension. The active component(s) is/are included in the pharmaceutical composition in therapeutic or preventive amounts, preferably in an amount of from 0.05 to 80 wt. %, based on the overall weight of the formulation.

The invention is also directed to the use of one or more of the allergens or nucleic acids according to the invention in the production of a drug for the desensitization to *A. versicolor*. Similarly, the genetically modified cells and microorganisms are used in the production of a drug for the desensitization to *A. versicolor*.

As part of the desensitization measures it is possible to use single allergens or a plurality of allergens. In this method, patients reacting allergically to proteins from *Aspergillus versicolor* are contacted with low doses of the allergens according to the invention. In this method, accustoming to such a low-dosed exposition results in a reduction of the allergic symptoms upon recontacting with *A. versicolor* or spores thereof.

A preferred method for the desensitization to *A. versicolor* uses proteins selected from the group comprising a glyceraldehyde-3-phosphate dehydrogenase (GAPDH; Asp a, b, c) with the amino acid sequence SEQ ID No. 1 or parts thereof as long as these parts are not identical to parts of the amino acid sequence of GAPDH of *Aspergillus fumigatus*, a hypothetical xylol/sorbitol reductase with the amino acid sequence SEQ ID No. 3 or parts thereof as long as these parts are not identical to parts of the amino acid sequence of the corresponding protein of *Aspergillus fumigatus* having the genebank accession number gi/71002394/ref/XP_755878.1, a katalase A with a molecular weight of 84,108 Daltons and an isoelectric point of 6.02 (Asp e), a protein with a molecular weight of 26,713 Daltons and an isoelectric point of 6.53 (Asp f), an enolase with a molecular weight of 47,519 Daltons and an isoelectric point of 5.37 (Asp g), a protein with a molecular weight of 22,007 Daltons and an isoelectric point of 5.85 (Asp h), a malate dehydrogenase with a molecular weight of 35,764 Daltons and an isoelectric point of 8.82 (Asp i).

Without intending to be limiting, the invention will be illustrated in more detail below with reference to the examples.

EXAMPLES

Identification of Allergens from *A. versicolor*

A precondition for identifying allergens and detecting sensitization of patients is the presence of specific serum IgEs targeted to proteins of *A. versicolor*. Reactivity is detected on blot membranes loaded with electrophoretically separated proteins of *A. versicolor*. A band or spot is detected in a subsequent immunostaining using secondary anti-IgE antibodies (coupled to alkaline phosphatase), and each one represents an allergenic protein.

BRIEF DESCRIPTION OF THE DRAWINGS

The invention will now be described in greater detail with reference to the drawings, wherein:

FIG. 1 shows 2D and 1D immunostaining of a patient exhibiting specific reaction to spore proteins of *A. versicolor*. The marked area represents protein spots most frequently detected in 2D immunostaining.

A.v.=*Aspergillus versicolor*, A.f.=*Aspergillus fumigatus*, P.e.=*Penicilium expansum*.

Initial analysis of patient serums using 1D immunostaining showed positive reaction to allergen extracts of the molds *A. versicolor, A. fumigatus* or *P. expansum* in 47 out of 100 patients who had attended treatment for general allergic symptoms. Conspicuously, there was not even one patient serum that reacted exclusively to *A. fumigatus* or *P. expansum* (see FIG. 2). However, among the 47 positive patient serums there were 31 serums that reacted to all mold extracts, while 8 serums reacted only to *A. versicolor*. These data demonstrate that a test based on extracts of *A. fumigatus* or *P. expansum* does not automatically detect sensitization to *A. versicolor*.

Figure 1:
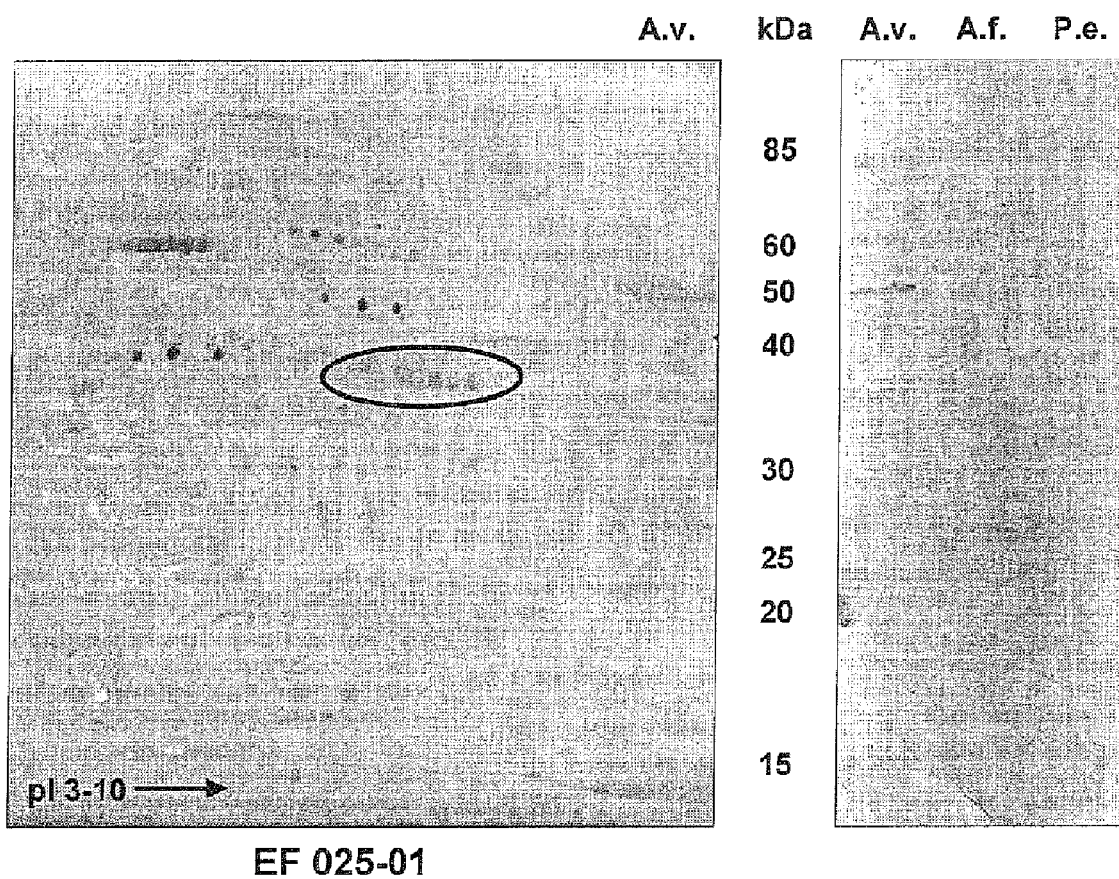
FIG. 1 shows immunostaining of a patient exhibiting a specific reaction to spore proteins of *A. versicolor*.
Figure 2:
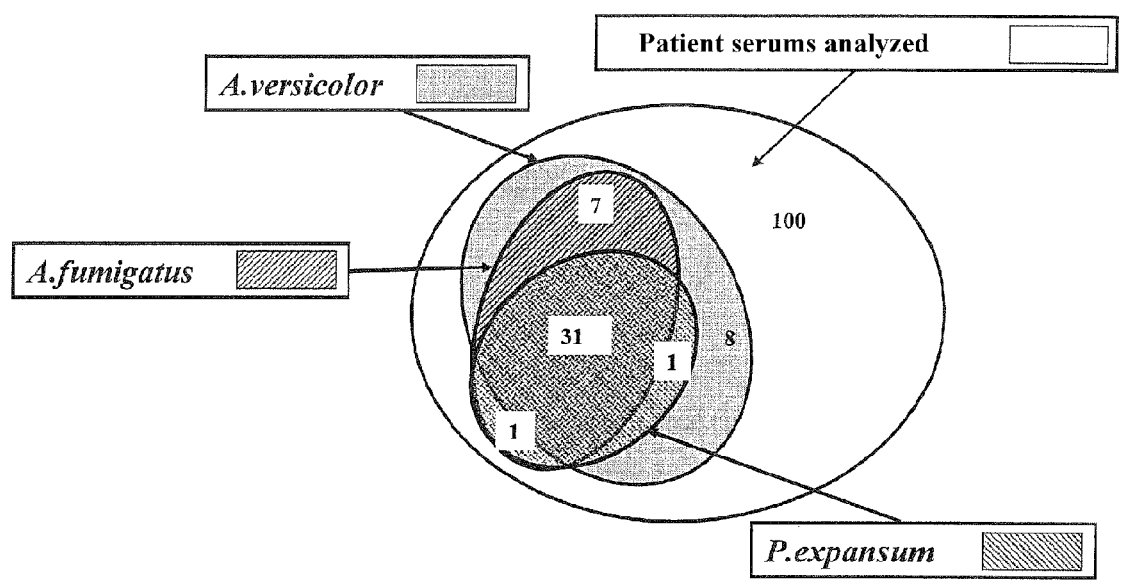
FIG. 2 shows an intersection diagram to illustrate the reactivity of patient serums to spore proteins of *A. versicolor, A. fumigatus* and *P. expansum*.

FIG. 2 shows an intersection diagram to illustrate the reactivity of patient serums to the spore proteins of the molds *A. versicolor, A. fumigatus* and *P. expansum* in 1D immunostaining, wherein the numbering corresponds to the number of reactive serums. Reaction only to *Aspergillus versicolor* (8, white), reaction only to *Aspergillus fumigatus* (0, shaded), reaction only to *Penicilium expansum* (0, mesh), reaction to *Penicilium expansum* and *Aspergillus fumigatus* (1), reaction to *Aspergillus versicolor* and *Penicilium expansum* (1), reaction to *Aspergillus versicolor* and *Aspergillus fumigatus* (7), reaction to all three molds (31), total number of patients (100, gray).

Immunodetection of Allergens

Here, detection of allergens via mediation of the patients' own IgE antibodies is the method of finding the allergens and simultaneously the proof of principle for a method of detecting sensitization of these patients based on the patients' own IgE antibodies. On the one hand, sensitization can be detected using the Western blot procedures described herein, but it is also possible to switch to the ELISA format. However, primary detection of the allergen proceeds via the patients' own IgE antibodies in the ELISA format as well.

Furthermore, the data obtained permit identification of allergens from spores of *A. versicolor*. For identification, the allergens that had been recognized were cut out of the 2D gels, tryptically digested, and the peptide masses as well as the fragment masses thereof were measured using mass spectrometry (see FIG. 3, cf. Table 1). The three major allergens were found in more than 70% of the patients analyzed and showed the strongest reaction intensity in 2D immunostaining. Similarly, the four other allergens were found in more than 50% of the patients.

Figure 3:
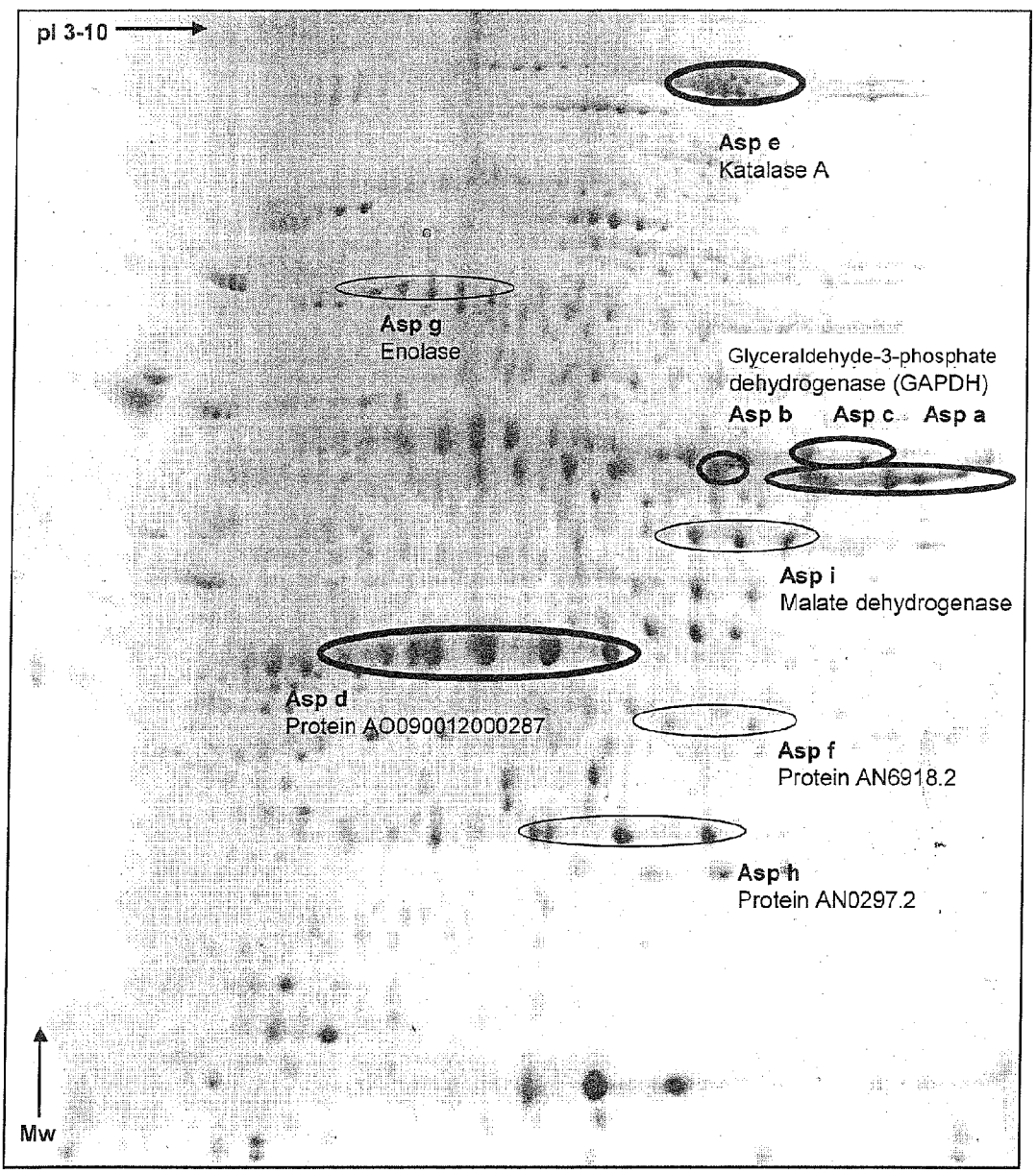
FIG. 3 shows the proteins of *A. versicolor* separated according to their isoelectric points and molecular weights.

FIG. 3 shows the proteins of *A. versicolor* separated according to isoelectric point and molecular weight in a 2D gel. Table 1 summarizes the characterization of the allergens found.

TABLE 1

| Designation of allergen | Name of allergen | Isoelectric point | Molecular weight (Daltons) |
|---|---|---|---|
| Asp a, b, c | Glyceraldehyde-3-phosphate dehydrogenase (GAPDH) | 6.97 | 36,389 |
| Asp d | Protein AO090012000287 | 6.11 | 28,784 |
| Asp e | Katalase A | 6.02 | 84,108 |
| Asp f | Protein AN6918.2 | 6.53 | 26,713 |
| Asp g | Enolase | 5.37 | 47,519 |
| Asp h | Protein AN0297.2 | 5.85 | 22,007 |
| Asp i | Malate dehydrogenase | 8.82 | 35,764 |

The invention claimed is:

1. An isolated allergen of *Aspergillus versicolor*, wherein said allergen is glyceraldehyde-3-phosphate dehydrogenase (GAPDH) with the amino acid sequence SEQ ID No. 1.

2. A pharmaceutical composition comprising a desensitizing amount of an allergen according to claim 1.

3. An isolated nucleic acid comprising at least one sequence which encodes an allergen of *Aspergillus versicolor*, wherein said nucleic acid encodes glyceraldehyde-3-phosphate dehydrogenase (GAPDH) with the amino acid sequence SEQ ID No. 1.

4. A method for the in vitro detection of a mold allergy to *Aspergillus versicolor*, comprising detecting *A. versicolor*-specific IgE and/or IgG antibodies in a sample of body fluid by binding to the allergen of *A. versicolor* according to claim 1.

5. The method according to claim 4, wherein detecting proceeds in an enzyme immunoassay or a radioimmunoassay.

6. The method according to claim 4, wherein detecting proceeds in an ELISA.

7. The method according to claim 4, wherein the body fluid is blood, serum, plasma, urine, cerebrospinal fluid, or saliva.

8. An isolated cell or a microorganism genetically modified to comprise the nucleic acid according to claim 3.

* * * * *